(12) United States Patent
Schwotzer et al.

(10) Patent No.: US 8,615,128 B2
(45) Date of Patent: Dec. 24, 2013

(54) METHOD FOR 3D, MEASUREMENT OF THE SURFACE OF AN OBJECT, IN PARTICULAR FOR DENTAL PURPOSES

(75) Inventors: Axel Schwotzer, Groβ-Gerau (DE); Konrad Klein, Heidelberg (DE)

(73) Assignee: Sirona Dental Systems GmbH, Bensheim (DE)

( * ) Notice: Subject to any disclaimer, the term of this patent is extended or adjusted under 35 U.S.C. 154(b) by 273 days.

(21) Appl. No.: 13/141,605

(22) PCT Filed: Dec. 23, 2009

(86) PCT No.: PCT/EP2009/067861
§ 371 (c)(1),
(2), (4) Date: Sep. 12, 2011

(87) PCT Pub. No.: WO2010/072816
PCT Pub. Date: Jul. 1, 2010

(65) Prior Publication Data
US 2011/0311105 A1    Dec. 22, 2011

(30) Foreign Application Priority Data

Dec. 24, 2008   (DE) .......................... 10 2008 055 158

(51) Int. Cl.
*G06K 9/00*   (2006.01)
(52) U.S. Cl.
USPC .......................................... 382/154; 382/106
(58) Field of Classification Search
USPC ................................................ 382/106, 154
See application file for complete search history.

(56) References Cited

U.S. PATENT DOCUMENTS

| 3,287,562 A | 11/1966 | Connors, Jr. et al. |
| 4,575,805 A | 3/1986 | Moermann et al. |
| 4,837,732 A | 6/1989 | Brandestini et al. |

(Continued)

FOREIGN PATENT DOCUMENTS

| DE | 10 2005 043 402 A1 | 3/2007 |
| EP | 0 250 993 A2 | 1/1988 |

(Continued)

OTHER PUBLICATIONS

European Patent Office, International Search Report and Written Opinion of the International Searching Authority issued in connection with International Application No. PCT/EP2009/067516, dated Apr. 29, 2010, 14 pages.

(Continued)

*Primary Examiner* — Uptal Shah
(74) *Attorney, Agent, or Firm* — Fitzpatrick, Cella, Harper & Scinto

(57) ABSTRACT

For the purpose of 3D scanning the surface of an object by optical double triangulation using the phase-shifting method, more particularly for dental purposes, at least two 3D scans of the same object (1) are carried out at different triangulation angles (θ1, θ2), the first angle of which is known and the second angle of which is known at least approximately. For each pixel ($B_i$) of the phase related image ($\phi1(x,y)$), a wave number ($wz(x_i,y_i)$) is determined using the second phase related image, the integral portion of which is equal to the order (n) of the uniqueness range (E1) in which the respective pixel ($B_i$) is located. The wave number ($wz(x,y)$) is optimized, at least for a random sample of m pixels ($B_i$), by minimizing a non-integral portion of the wave number ($wz(x_i,y_i)-[wz(x_i,y_i)]$).

8 Claims, 2 Drawing Sheets

(56) References Cited

U.S. PATENT DOCUMENTS

| | | | |
|---|---|---|---|
| 5,175,601 A * | 12/1992 | Fitts | 356/604 |
| 5,579,361 A | 11/1996 | Augais et al. | |
| 5,635,728 A | 6/1997 | Cantu et al. | |
| 6,040,910 A | 3/2000 | Wu et al. | |
| 6,822,745 B2 * | 11/2004 | De Groot et al. | 356/496 |
| 6,885,464 B1 * | 4/2005 | Pfeiffer et al. | 356/602 |
| 7,315,643 B2 * | 1/2008 | Sakamoto et al. | 382/154 |
| 2002/0085273 A1 | 7/2002 | Ito | |
| 2004/0151369 A1 * | 8/2004 | Schwotzer | 382/154 |
| 2007/0115484 A1 | 5/2007 | Huang et al. | |
| 2007/0188769 A1 | 8/2007 | Rohaly et al. | |
| 2008/0094631 A1 | 4/2008 | Jung et al. | |
| 2008/0239288 A1 | 10/2008 | Lee et al. | |
| 2009/0181346 A1 | 7/2009 | Orth | |
| 2009/0263115 A1 | 10/2009 | Suzuki et al. | |
| 2010/0157019 A1 | 6/2010 | Schwotzer et al. | |
| 2010/0158490 A1 | 6/2010 | Pfeiffer et al. | |
| 2010/0284589 A1 | 11/2010 | Thiel et al. | |

FOREIGN PATENT DOCUMENTS

| | | |
|---|---|---|
| EP | 0968687 A2 | 1/2000 |
| EP | 0 987 542 A2 | 3/2000 |
| EP | 1 908 399 A1 | 4/2008 |
| JP | 2002-090650 A | 3/2002 |
| JP | 2006-322949 A | 11/2006 |

OTHER PUBLICATIONS

International Search Report and Written Opinion of the International Searching Authority issued in the corresponding application No. PCT/EP2009/067516 dated Apr. 29, 2010.

European Patent Office, International Preliminary Report on Patentability in connection with International Application No. PCT/EP2009/067861, completed Apr. 6, 2011, 11 pages (and English translation thereof).

Pfeiffer, J., et al., "Dreidimensional optische Vermessung von Zahnen", Technisches Messen 63, Jun. 1996, pp. 254-261.

* cited by examiner

METHOD FOR 3D, MEASUREMENT OF THE SURFACE OF AN OBJECT, IN PARTICULAR FOR DENTAL PURPOSES

TECHNICAL FIELD

The invention relates to a method for 3D scanning the surface of an object by means of optical double triangulation using the phase-shifting method, more particularly to a method for improving the measuring accuracy of a 3D camera operating according to the principle of double triangulation using the phase-shifting method, particularly for dental purposes. The invention further relates to the improvement of the quality of the scanned 3D data sets evaluated.

PRIOR ART

U.S. Pat. No. 4,575,805 discloses a process for optical 3D scanning of objects, more particularly teeth, which process makes use of the triangulation method. For the phase-shifting method used in said citation, U.S. Pat. No. 6,040,910 discloses an algorithm for computing the phase related image from at least three images of a pattern projected onto an object.

EP 0 968 687 A2 discloses a scanning camera for detecting surface structures, particularly for dental purposes, by means of which scanning camera a 3D scan of the same object of interest is carried out at least twice in quick succession, the triangulation angle being altered slightly between the two scans. The difference between the measured values is used in order to increase the uniqueness range of the first recording.

The measuring accuracy of the camera when determining the uniqueness range depends on the ability to reproduce the alteration of the triangulation angle and thus the accuracy with which the triangulation angle is known. In the case of complete reproducibility of the second triangulation angle, the scanning camera can achieve high measuring accuracy by way of calibration. In the case of limited reproducibility, deviations of the second triangulation angle from the predefined triangulation angle used for determining the uniqueness range can lead to an incorrect assignment of the uniqueness range and thus to an erroneous relief value. Attempts have therefore been made in the prior art to ensure good reproducibility of the second triangulation angle to the best extent possible.

Furthermore, the second scan, due to possible inaccuracies, is likely to be used only for determining the uniqueness range, but not as an independent scan.

It is an object of the invention to further reduce the errors resulting from inadequate reproducibility of the second triangulation angle when determining the relief values. Furthermore, it is desirable for the second scan to be itself useful for acquiring a 3D data set.

SUMMARY OF THE INVENTION

According to the invention, a 3D data set of an object, more particularly, of one or more teeth, is generated by means of optical double triangulation using the phase-shifting method. For this purpose, a 3D scan of the same object is carried out at least twice at different triangulation angles that yield at least one phase related image for each triangulation angle, which phase related image comprises a plurality of pixels having coordinates, the first triangulation angle being known and the second triangulation angle being known at least approximately. Each phase related image has a uniqueness range that depends, inter alia, on the respective triangulation angle.

For each pixel of the first phase related image, a wave number is determined using the second phase related image, the integral portion of which wave number is equal to the order of the uniqueness range in which the respective pixel is located. This wave number is optimized at least for a sample of m pixels by minimizing a non-integral portion of the wave number.

The optimized wave number can be used for acquiring a relief image of the object or to determine the ratio of scaling factors that map the phase related images onto metric relief values, and to determine a drift between the two phase related images and to use the same as initial values for the optimization of an additional relief image or for creating a second metric relief image from the second phase related image.

By reason of insufficient reproducibility of the second triangulation angle, the second triangulation angle can be known only approximately. Thus, for the purpose of producing a second triangulation angle, the centroid of the illuminating beam can be shifted by means of an optical diaphragm. If this step is carried out mechanically, the reproducibility of the second triangulation angle can be error-prone.

As is disclosed in the prior art, the phase related images can each be formed from a plurality of images of a periodic pattern that is projected onto an object, which pattern has a known phase position shifted in relation to the respective preceding image.

The correlation between a phase shift of the pattern in relation to a reference and to the corresponding phase image is given by a unique periodic function.

If the height range of the scanning range is larger than the uniqueness range, then the mapping of the phase related images onto metric relief values is equivocal. However, it is known from the prior art that, on account of the difference between two phase related images at any one pixel, an order of the uniqueness range in which the pixel is located, can be assigned to this pixel, in order to eliminate equivocality.

Advantageously, the pattern projected onto the object has a sinusoidal brightness distribution having a known shiftable phase position. This makes it possible to use known evaluation algorithms.

Advantageously, the first scaling factor that maps the first phase related image onto metric relief values is known accurately, and the second scaling factor that maps the second phase related image onto metric relief values is known at least approximately.

These scaling factors can be determined by calibrating the system prior to scanning the object and are proportional to the tangent of the respective triangulation angle.

If the integral portions of the wave numbers for at least two pixels $B_i$ are different for the recorded pair of phase related images, the wave number can be advantageously optimized, at least for a sample of m pixels, by minimizing a non-integral portion of the wave number by altering the ratio of the scaling factors via the at least approximately known scaling factor and by altering the drift of the phase position of the pattern between the two phase related images.

This full optimization procedure makes it possible to reduce errors when assigning the order of the uniqueness range to a pixel and thus to acquire the relief image more efficiently.

This optimization procedure also improves determination of the second triangulation angle. Thus the dimensional accuracy of the second recording can also be achieved without additional calibration by means of a calibration member. This optimization procedure is thus a self-calibrating process.

If the integral portions of the wave number for all pixels are identical in the recorded pair of phase related images, the wave number can be advantageously optimized by minimizing the non-integral portion of the wave number, at least for a sample of m pixels, by altering the drift between the two phase related images.

By means of this portionial optimization procedure, at least the error that falsifies the wave number by reason of a drift of the pattern and that thus results in error-prone relief values can be corrected.

For the sample of m pixels, error-prone pixels can be advantageously eliminated from the phase related images on the basis of the quality of the measured data and a suitable outlier-recognition process, the pixels of the sample being located particularly within an expected distribution in terms of the non-integral portion of the distribution.

Suitable selection of the sample includes measured values from the central image area, which is usually located within the scanning range, and not from the border area of the images. This, in combination with the elimination of erroneous pixels, leads to improved results of the optimization procedure.

For outlier recognition, for example, it is possible to use the modulation amplitude of the projected sine pattern sequence in the phase related image in that the actual distribution of the amplitudes is compared with an expected distribution.

Advantageously, the first and second phase related images can be recorded in quick succession, the advantage of this being that the position of the camera, particularly when using a handheld camera, is not altered or is altered only slightly between recordings.

For creating an improved second relief image from the second phase related image, both the scaling factor of the second phase related image, which scaling factor is known only inaccurately, and a positional change of the camera between the second relief image and the first relief image obtained using the optimized wave number can be allowed for to advantage in an optimization procedure using the first relief image obtained from the optimization, the positional change of the camera being assumed to be due to rotary and translational movements.

This has the advantage that the second phase related image can also be used as an adequate exposure for producing a relief image in spite of the uncertainty of the actual triangulation angle.

BRIEF DESCRIPTION OF THE DRAWINGS

An exemplary embodiment of the invention is explained below with reference to the drawings, in which.

EXEMPLARY EMBODIMENT

Figure 1:
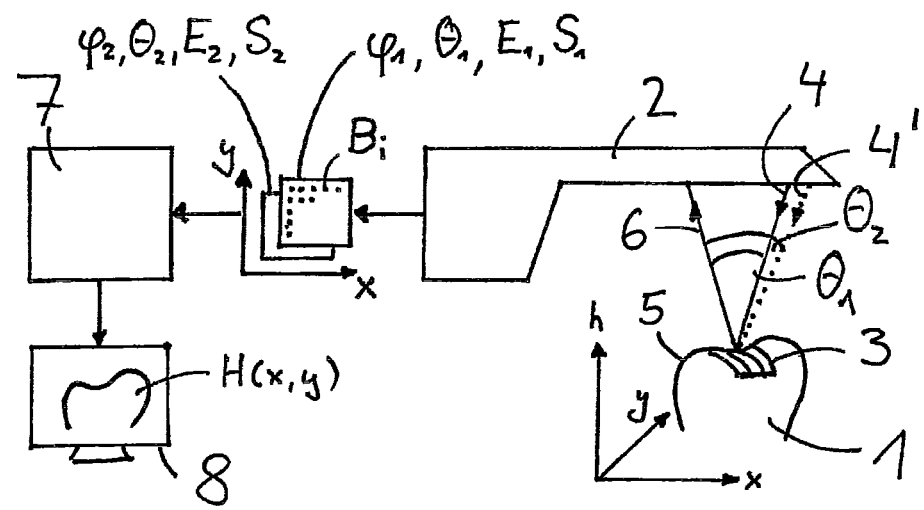
FIG. 1 is a diagram illustrating the method of the invention carried out by means of a 3D camera and an image-processing unit.

As represented diagrammatically in FIG. 1, a periodic pattern 3 having a known phase relationship is projected by an illuminating beam 4 or 4' onto a portion of the surface 5 of an object 1 and is imaged by means of a 3D camera 2 when carrying out 3D scanning of the object 1 by means of double triangulation using the phase-shifting method.

The intensity of the light scattered by the surface 5 of the object 1 having the pattern 3 imaged thereon is recorded for pixels $B_i$ having the coordinates $x_i$ and $y_i$ in a monitoring direction 6 that encloses a triangulation angle $\theta 1$ with the illuminating beam 4, and a triangulation angle $\theta 2$ with the illuminating beam 4'. When the triangulation angle $\theta 1$ is known and the triangulation angle $\theta 2$ is known only approximately, possibly because the angle $\theta 2$ is not accurately reproducible, the second recording can be used only to a limited extent, since it is error-prone.

From a number of intensities for different phase relationships of the pattern recorded at each of the triangulation angles $\theta 1$ and $\theta 2$, a phase can be determined for the individual pixels $B_i$. The sum of these phases is referred to hereinafter as raw phase image p1(x,y) for images recorded at the triangulation angle $\theta 1$, and as raw phase image p2(x,y) for images recorded at the second triangulation angle $\theta 2$.

Furthermore, there can be reference images r1(x,y) and r2(x,y) known as a result of a calibration of the system, which reference images are phase related images of the pattern projected onto a flat surface extending normal to the camera visual axis, which phase related images are each recorded using the corresponding triangulation angle. These reference images r1 and r2 can be deducted from the phase image p1(x,y) and p2(x,y) respectively, and this difference is equal to a phase shift of the phase image p1(x,y) and p2(x,y) relative to the reference image r1(x,y) and r2(x,y) at any one pixel $B_i$ and is proportional to the relief of the surface of the object at this pixel $B_i$.

Since the phases of the recorded raw phase images p1(x,y) and p2(x,y) are unequivocal only within a range of $[0.2\pi]$, the difference between the raw phase image p1(x,y) or p2(x,y) and the reference image r1(x,y) or r2(x,y) respectively can therefore also be limited to the range $[0.2\pi]$ and is referred to hereinafter as phase related image $\phi1(x,y)$ or also as an orthogonalized phase related image.

The phase related images $\phi1$ and $\phi2$ are mapped onto relief images H1 and H2 by means of scaling factors S1 and S2 that are known from calibration of the system carried out at the respective triangulation angle $\theta 1$ and $\theta 2$ prior to scanning the object. Since the triangulation angle $\theta 2$ is reproducible only approximately, the scaling factor S2 is error-prone.

An relief value h can be assigned unequivocally to a phase of the phase related images $\phi1(x,y)$ and $\phi2(x,y)$ only within a respective uniqueness range E1 and E2 respectively that depends both on the triangulation angle $\theta 1$, $\theta 2$ and on the period of the pattern.

If the relief range to be scanned is larger than the uniqueness range E1 or E2, then the assignment of relief values h to the respective phase related image $\phi1$ and $\phi2$ respectively is equivocal.

The relief image is acquired in an image-processing unit 7 and can be displayed on an output unit 8. The process of acquiring the relief image is illustrated more distinctly in FIGS. 2 to 4.

Figure 2:
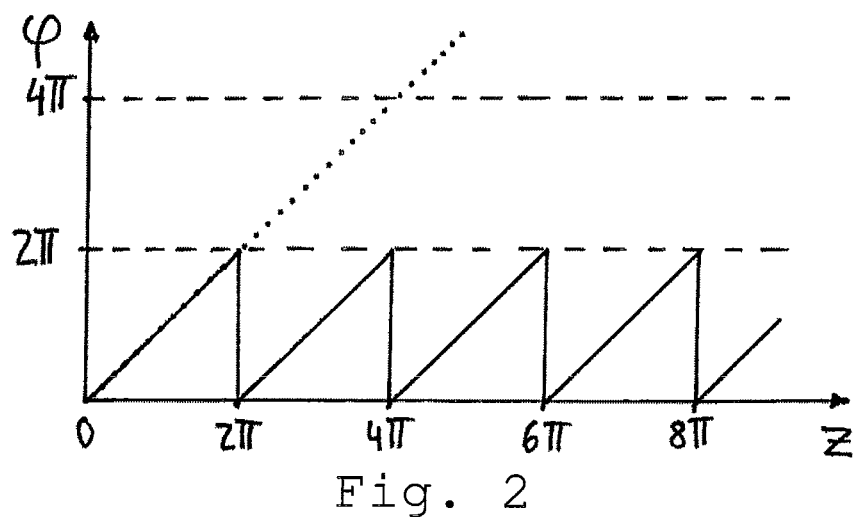
FIG. 2 shows the correlation between phase shift and phase related image.

FIG. 2 shows the correlation between a real phase shift z that is not limited to the range $[0.2\pi]$ and that indicates the shift between the phase of the pattern imaged on the object and the phase of the reference images r1(x,y) and r2(x,y) at a pixel $B_i$, and the phase related images $\phi1(x,y)$ and $\phi2(x,y)$, which correlation has the shape of a saw tooth with a period length of $2\pi$ and an amplitude of likewise $2\pi$. This correlation results from the equivocality of the phase related images $\phi1(x,y)$ and $\phi2(x,y)$.

Figure 3:
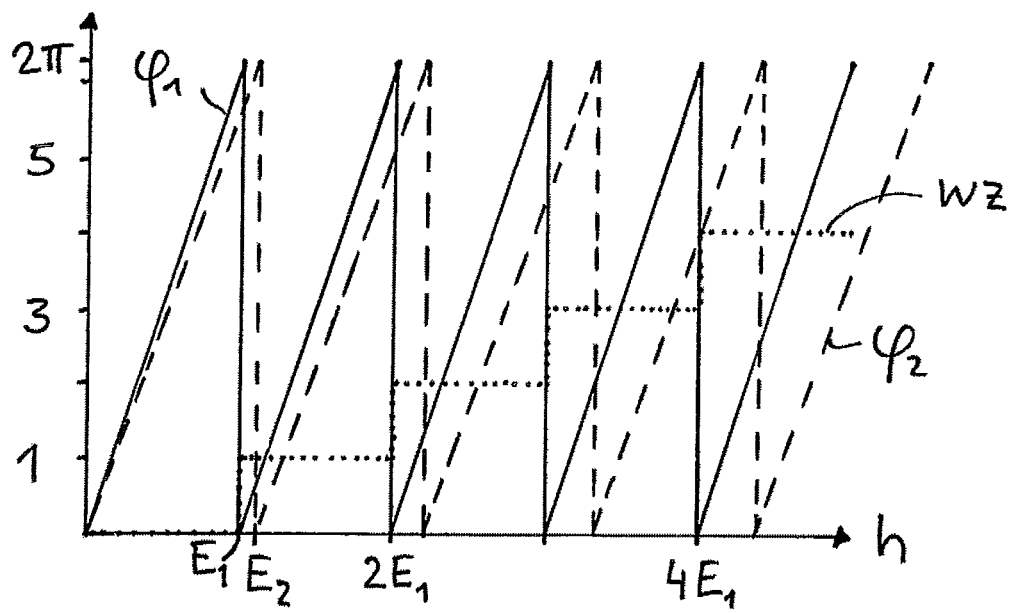
FIG. 3 shows the correlation between relief values and phase related images, and the idealized correlation between the relief values and the wave number.

FIG. 3 shows the correlation between the phases of respective phase related images $\phi1(x,y)$ and $\phi2(x,y)$ and the relief values h, which correlation results from the equivocality of the phase related images φ1(x,y) and φ2(x,y). The period length of the respective saw tooth is equal to the respective uniqueness range E1 and E2 respectively.

It is evident that the difference between the phase images φ1(x,y) and φ2(x,y) also increases as the relief values h increase. This difference between the phase related images φ1(x,y) and φ2(x,y) allows a conclusion to be drawn on the order n in which the phase of a phase related image φ1($x_i$,$y_i$) measured at a pixel $B_i$ is located. This is disclosed in EP 0 968 687 A2.

For every pixel, a wave number wz can be computed using a scaled difference between the phase related images φ1 and φ2, which wave number wz is equal to the order of the uniqueness range of the pixel of the first phase related image φ1. The formula for computing the wave number wz is as follows:

$$wz=((r*φ1-φ2)\bmod(2π))/(2π*(1-r)),$$

where r indicates the ratio between the two scaling factors S1 and S2. In the case of an error-free measurement of the phase related images φ1, φ2 and with error-free scaling factors S1 and S2, the wave number is always an integer. The resulting stepped profile of this wave number as a function of the relief values h, which is likewise shown in FIG. 3, thus corresponds to an idealized profile.

Figure 4:
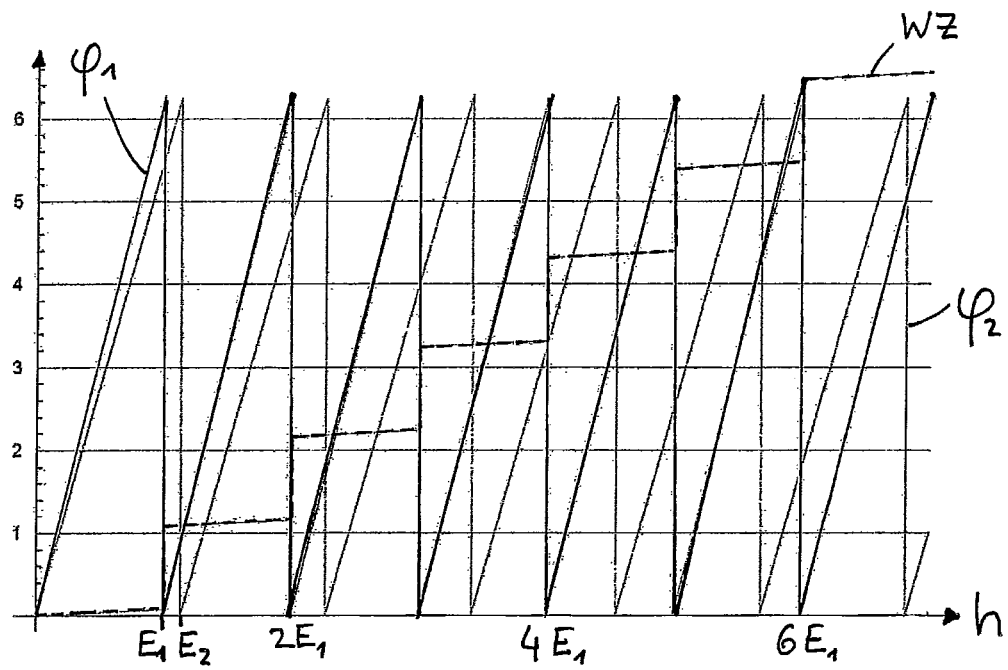
FIG. 4 shows the correlation between the relief values and the wave number for real 3D scanning.

FIG. 4 shows a real profile of the wave number that is acquired using an error-prone scaling factor S2. The error of the scaling factor results in an error of the wave number, which error increases continually as the relief value h increases. Thus the wave number no longer assumes only integral values, but instead has a non-integral portion that increases continually as the relief value h increases so that the steps of the stepped profile of the correlation between relief values h and the wave number wz are no longer flat, but instead have a nonzero slope. Auxiliary horizontal lines are drawn in FIG. 4 to indicate the slope of the individual steps.

A drift of the pattern between the scanning of the two phase related images φ1, φ2 can also result in an error when acquiring the wave number wz. Such an error leads to a constant upward or downward misalignment of the profile of the wave number depending on the relief. Such an error would displace the stepped profile shown in FIGS. 3, 4 in an upward or downward direction, but it does nothing to change the profile of the individual steps themselves.

The error of the input parameters can be read from the deviation from the ideal stepped profile of the wave number, that is, from the non-integral portion of the wave number, and this deviation can be minimized by means of an optimization procedure. For this purpose, the non-integral portion of the wave number wz can be minimized using the method of the least square error in that both the ratio r can be altered by means of the scaling factor S2 and the drift q between the phase positions of the pattern in the two phase related images φ1 and φ2 can be altered when it is desired to minimize the square error. For this purpose, the integral portions of at least two wave numbers wz of the phase related images φ1 and φ2 must differ from each other.

If the integral portions of all wave numbers wz of the two phase related images φ1 and φ2 are identical, the non-integral portion of the wave numbers can be minimized in an optimization procedure by altering the drift q between the phase positions of the pattern in the two phase related images φ1 and φ2.

The relief values h of the relief image H1(x,y) can be acquired from the phase related image φ1(x,y) in that, for each pixel $B_i$, the 2π-fold optimized wave number wz(x1, y1) is added to the phase related image φ1($x_i$,$y_i$), and the sum thereof is multiplied by a scaling factor S1.

The optimizing procedures described are suitable for acquiring the wave number wz with the required degree of rereliability and to effectively eliminate the equivocality of the phase related images φ1 and φ2.

A second relief image H2 of the object can be created from the second phase related image φ2 by the use of an additional optimizing procedure. For this purpose, the difference between the two relief images H1 and H2 can be minimized using a method of the least square error in that both the optimized scaling factor S2 is further optimized and a positional change of the camera due to rotary and translational movements of the first relief image H1 are allowed for.

LIST OF REFERENCE NUMERALS AND CHARACTERS 1 object
2 3D camera
3 pattern
4 illuminating beam
5 surface of the object
6 monitoring direction
7 image processing unit
8 output unit
θ triangulation angle
φ phase related image
Bi pixel
S scaling factor
E uniqueness range
Z phase shift
h metric relief value
H relief image
wz wave number

The invention claimed is:

1. A method for 3D scanning of a surface of an object by means of optical double triangulation using a phase shifting process, the method comprising:
   performing at least two 3D scans of the object at different triangulation angles (θ1, θ2) yielding for each triangulation angle (θ1, θ2) at least one phase related image (φ1(x,y), φ2(x,y)) containing a plurality of pixels ($B_i$) with coordinates ($x_i$,$y_i$), wherein a first one of the triangulation angles is known and a second one of the triangulations angle is at least approximately known, and each phase related image (φ1(x,y), φ2(x,y)) has a uniqueness range (E1, E2) depending, inter alia, on at least one of the triangulation angles (θ1, θ2),
   for each pixel ($B_i$) in a first phase related image (φ1(x,y)), determining a wave number using a second phase related image (φ2(x,y)) whose integral portion is equal to an order (n) of the uniqueness range (E1) in which at least one respective pixel ($B_i$) is located,
   optimizing the wave number such that at least for a random sample of m pixels ($B_i$) a non-integral portion of the wave number is minimized, and
   performing at least one of the following based on the optimized wave number:
      determining a relief image (H1(x,y)) of said object, by forming, for each pixel ($B_i$), a sum of the phase related image (φ1($x_i$,$y_i$)) at this pixel ($B_i$) and 2n times a corresponding wave number and multiplying the sum by a scaling factor (S1),
      determining a ratio (r) of scaling factors (S1, S2) which map the phase related images (φ1,φ2) onto metric relief values h and determining a drift (q) between a phase position of a pattern in the phase related images (φ1(x,y), φ2(x,y)) for use as initial values for optimization of a next relief image (H(x,y)) during a next 3D scan of said object, or creating a second metric relief image (H2(x,y)) from the second phase related image (φ2(x,y)).

2. The method as defined in claim 1, further comprising, for execution of said phase shifting method, projecting a pattern onto the object, which pattern has a sinusoidal brightness distribution having a known displaceable phase position.

3. The method as defined in claim 1, wherein the first scaling factor (S1) is known, which maps said first phase related image (φ1) onto the metric relief values h, and that a second one of the scaling factors (S2) is known at least approximately, which maps said second phase related image (φ1) onto the metric relief values h.

4. The method as defined in claim 1, further comprising, if, for the phase images (φ1(x,y), φ2(x,y)) recorded for at least two pixels, an integral portion of the wave number is different for these pixels $B_i$, optimizing the wave number such that, at least for a random sample of m pixels ($B_i$), a non-integral portion of the wave number is minimized by altering the ratio (r) of the scaling factors (S1, S2) via the at least approximately known scaling factor (S2) and by altering the drift (q) of said pattern between the phase related images (φ1(x,y), φ2(x,y)).

5. The method as defined in claim 1, further comprising, if, for the recorded pair of phase related images (φ1(x,y), φ2(x,y)), integral portions of the wave number are the same for all pixels ($B_i$), optimizing the wave number in such a manner that at least for a random sample of m pixels ($B_i$) a non-integral portion of the wave number is minimized by altering the drift (q) between the phase related images (φ1(x,y), φ2(x,y)).

6. The method as defined in, claim 5, further comprising, for an m-element random sample, excluding defective pixels from said phase related images (φ1, φ2) on the basis of a quality of measured data and a suitable outlier recognition method, wherein the pixels of the random sample are within an expected distribution as regards the non-integral portion of the distribution.

7. The method as defined in claim 1, further comprising collecting images for the first and second phase related images in succession.

8. The method as defined in claim 1, further comprising, creating a second relief image (H2) from said second phase related image (φ2) in an optimizing procedure implementing a first relief image (H1(x,y)) resulting from optimizing both the approximately known scaling factor (S2) and a change of position of a camera between the phase related images (φ1) and (φ2), while the change of position of the camera is assumed to be due to rotary and translational movements.

\* \* \* \* \*